(12) United States Patent
Fukushima et al.

(10) Patent No.: US 9,150,595 B2
(45) Date of Patent: Oct. 6, 2015

(54) PROCESS FOR PRODUCING SILANE COUPLING AGENT

(75) Inventors: Yasuo Fukushima, Kodaira (JP); Satoshi Horie, Kodaira (JP)

(73) Assignee: BRIDGESTONE CORPORATION, Tokyo (JP)

( * ) Notice: Subject to any disclaimer, the term of this patent is extended or adjusted under 35 U.S.C. 154(b) by 66 days.

(21) Appl. No.: 13/392,411

(22) PCT Filed: Aug. 26, 2010

(86) PCT No.: PCT/JP2010/005282
§ 371 (c)(1),
(2), (4) Date: Feb. 24, 2012

(87) PCT Pub. No.: WO2011/024466
PCT Pub. Date: Mar. 3, 2011

(65) Prior Publication Data
US 2012/0149929 A1    Jun. 14, 2012

(30) Foreign Application Priority Data

Aug. 26, 2009  (JP) .................................. 2009-195993

(51) Int. Cl.
*C07F 7/10* (2006.01)
*C07F 7/18* (2006.01)

(52) U.S. Cl.
CPC ............... *C07F 7/1836* (2013.01); *C07F 7/184* (2013.01)

(58) Field of Classification Search
None
See application file for complete search history.

(56) References Cited

U.S. PATENT DOCUMENTS

| | | | |
|---|---|---|---|
| 3,842,111 A | 10/1974 | Meyer et al. | |
| 3,873,489 A | 3/1975 | Thurn et al. | |
| 7,375,170 B2 * | 5/2008 | Oikawa et al. ................ | 526/194 |
| 2010/0120950 A1 | 5/2010 | Saiki et al. | |

FOREIGN PATENT DOCUMENTS

| | | |
|---|---|---|
| DE | 102005004676 A1 | 8/2006 |
| EP | 2246355 A1 | 11/2010 |
| EP | 2433945 A1 | 3/2012 |
| JP | S58131991 A | 8/1983 |
| JP | H02273686 A | 11/1990 |
| JP | 8-311078 A | 11/1996 |
| JP | H0925282 A | 1/1997 |
| JP | 2002-284787 A | 10/2002 |
| JP | 2008-169157 A | 7/2008 |
| JP | 2008184464 A | 8/2008 |
| RU | 2291871 C1 | 1/2007 |
| WO | 2008/082011 A1 | 7/2008 |
| WO | 2008/084885 A1 | 7/2008 |

OTHER PUBLICATIONS

Grant & Hackh's Chemical Dictionary (5th Ed. 1987) at p. 148.*
Notification of Reasons for Refusal issued Jan. 7, 2014 in corresponding Japanese Patent Application No. 2009-195993 with English translation.
Jacek Gulinski, et al., "Synthesis of organofunctional silanes with sterically hindered substituents at silicon atoms", Applied Organometallic Chemistry, vol. 15, No. 8, 2001, pp. 649-657.
von Helmut Zoedler, et al., "181. Thallium compounds as catalysts for transesterification and ester exchange reactions", Helvetica Chimica Acta, vol. 60, No. 6, 1977, pp. 1845-1860.(English abstract only).
Extended European Search Report issued Jun. 28, 2013 in European Patent Application No. 10811522.1 to Bridgestone Corporation.
S.N. Gurkova, et al., "Crystal and Molecular Structure of 1-(cyclopropyl)silatrane", Journal of Structural Chemistry, vol. 29, No. 2, Jan. 1, 1988, pp. 345-348 (XP055054408).
V.M. D'Yakov, et al., "Acylation of 1,3-dioxa-6-aza-2-silacyclooctanes and Their 6-(trimethylsilyl) Derivatives with Alkyl Chloroformates", Russian Journal of General Chemistry, Pleiades publishing, Springer, Melville, NY, US, vol. 57, No. 2, Feb. 1, 1987 (XP008160410).
V.M. D'Yakov, et al., "Medium-Sized Silicon-Containing Rings. III. Carbo- and Silico-Functional Derivatives of 2-Organyl-1,3,6,2-Dioxazasilocanes and Their Reactions", Russian Journal of General Chemistry, Pleiades Publishing, Springer, Melville, NY, US, vol. 62, No. 2, Feb. 1, 1992 (XP008160411).
First Office Action issued Dec. 19, 2013 in corresponding Chinese Patent Application No. 201080048247.0 with English translation.
Voronkov et al., "Researches on Alkoxysilanes", Chemistry of Heterocyclic Compounds, vol. 2, No. 6, Nov. 1, 1966, pp. 671-681, ISSN:0009-3122.
Mazheika et al., "Nitrogen-Containing Organosilicon Compounds, XI. Dipole Moments and Structure of Some Azasilacyelanes", Chemistry of Heterocyclic Compounds, Jan. 1, 1968, vol. 4, No. 3, pp. 415-416.
Office Action dated Aug. 7, 2014, issued by the European Patent Office in European Application No. 10811522.1.
Office Action dated Jun. 5, 2014 issued from the State Intellectual Property Office of P.R. China in Chinese Patent Application No. 201080048247.0.
Communication dated Sep. 28, 2014 from the State Intellectual Property Office of the People's Republic of China in Chinese Patent Application No. 201080048247.0.
Communication dated Mar. 23, 2015 from the State Intellectual Property Office of People's Republic of China in corresponding Chinese Application No. 201080048247.0.

* cited by examiner

Primary Examiner — Michael Barker
Assistant Examiner — Po-Chih Chen
(74) Attorney, Agent, or Firm — Sughrue Mion, PLLC

(57) ABSTRACT

Provided is a process for producing a silane coupling agent, which can shorten the time required for the production process. A process for producing a silane coupling agent, characterized by comprising a step of reacting a silane compound (A) with a compound (B) which has a hydroxyl group and further contains an atom having an unshared electron pair other than an oxygen atom derived from the hydroxyl group, in the presence of a metal-containing catalyst (m) to obtain a silane compound (C) which has an alkoxyl group containing the atom having the unshared electron pair other than the oxygen atom derived from the hydroxyl group.

6 Claims, No Drawings

PROCESS FOR PRODUCING SILANE COUPLING AGENT

CROSS REFERENCE TO RELATED APPLICATIONS

This application is a National Stage of International Application No. PCT/JP2010/005282 filed Aug. 26, 2010, claiming priority based on Japanese Patent Application No. 2009-195993 filed Aug. 26, 2009 the contents of all of which are incorporated herein by reference in their entirety.

TECHNICAL FIELD

This invention relates to a process for producing a silane coupling agent, and relates to a process for producing a silane coupling agent which can shorten the time required for the production process.

BACKGROUND ART

In recent years, from the perspective of vehicle safety, improvement in safety of tires on wet road surfaces has been demanded. Moreover, from the perspective of reduction of carbon dioxide emissions along with a growing interest in environmental issues, further fuel efficiency of vehicles has also been demanded.

For these demands, conventionally, as a technique for simultaneously pursuing improvement in performance of tires on wet road surfaces and reduction in rolling resistance, a method of using an inorganic filler such as silica as a filler of a rubber composition for use in tire treads has been known to be effective. However, a rubber composition comprising an inorganic filler such as silica, which has a high viscosity in unvulcanized state and requires multistage kneading, while reducing the rolling resistance of tires, improving the braking property on wet road surfaces, and improving driving stability, has a problem in workability. Therefore, in the rubber composition comprising an inorganic filler such as silica, breaking strength and wear resistance significantly deteriorate, and problems such as delayed vulcanization and poor dispersion of fillers occur. Thus, when an inorganic filler such as silica is compounded in a rubber composition for treads, it is essential to add a silane coupling agent so as to decrease the viscosity in the unvulcanized state of the rubber composition, ensure the modulus and the wear resistance, and also further decrease the hysteresis loss.

PRIOR ART DOCUMENT

Patent Documents

Patent Document 1: U.S. Pat. No. 3,842,111
Patent Document 2: U.S. Pat. No. 3,873,489

SUMMARY OF THE INVENTION

Problem to be Solved by the Invention

However, since the silane coupling agent is expensive, the compounding cost increases by compounding the silane coupling agent. Moreover, also by the addition of a dispersion improver, the viscosity in the unvulcanized state of the rubber composition decreases and thereby the workability improves, but the wear resistance deteriorates. Furthermore, when the dispersion improver is a compound with high ionicity, the deterioration in the workability such as roll adhesion can also be seen. Still further, as the inventor has considered, it has become clear that even though a conventional silane coupling agent is added while compounding an inorganic filler such as silica as a filler, reduction in the hysteresis loss and improvement in the wear resistance of a rubber composition cannot reach a sufficiently satisfactory level, so room for improvement still remains.

In response to this, the inventors have newly discovered that it is particularly preferable to introduce a structure with an atom having an unshared electron pair into a silane coupling agent, from the perspective of improving the coupling efficiency with an inorganic filler. The silane coupling agent can be produced by reacting alcohol having an unshared electron pair with a silane compound. In this case, although the reaction time was assumed to be shortened by using an acid catalyst or a base catalyst, when an acid catalyst or a base catalyst was used, there were cases where no reaction occurred and the reaction time was slow in contradiction to the assumption, and it has become clear that there is still room for improvement.

Therefore, the object of the invention is to solve the above problems of the conventional technique and provide a process for producing a silane coupling agent which can shorten the time required for the production process.

Means for Solving the Problem

The inventors have, as a result of devoted examinations to achieve the above object, found out that an objective silane compound (C) can be produced in a shorter time at a higher yield by reacting a silane compound (A) with a particular compound (B) in the presence of a particular catalyst, and completed the invention.

That is, a process for producing a silane coupling agent of the invention is characterized by comprising a step of reacting a silane compound (A) with a compound (B) which has a hydroxyl group and further contains an atom having an unshared electron pair other than an oxygen atom derived from the hydroxyl group, in the presence of a metal-containing catalyst (m) to obtain a silane compound (C) which has an alkoxyl group containing the atom having the unshared electron pair other than the oxygen atom derived from the hydroxyl group.

Moreover, the metal-containing catalyst (m) is desirable to be a metal alkoxide.

Furthermore, a metal contained in the metal alkoxide is desirable to be at least one selected from the group consisting of lithium, sodium, potassium, rubidium, cesium, beryllium, magnesium, calcium, strontium, barium, boron, aluminum, gallium, indium, yttrium, titanium, zirconium, niobium, chromium, manganese, iron, cobalt, nickel, copper and zinc, and the metal-containing catalyst (m) is more desirable to be an aluminum alkoxide.

Also, a reaction temperature in the presence of the metal-containing catalyst (m) is desirable to be within a range of 50 to 200° C., and further, more desirable to be within a range of 90 to 170° C.

Also, a reaction time in the presence of the metal-containing catalyst (m) is desirable to be within a range of 0.5 to 6 hours.

Also, the atom having the unshared electron pair is desirable to be a nitrogen atom or an oxygen atom, and further, more desirable to be the nitrogen atom.

Also, the silane compound (C) is desirable to be represented by the following general formula (I):

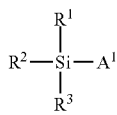
(I)

[In the formula (I), $A^1$ is a monovalent group, and
at least one of $R^1$, $R^2$ and $R^3$ is represented by the following general formula (Ia) or formula (Ib):

[Chem. 2]

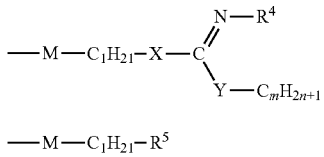

(In the formulae (Ia) and (Ib), M is —O— or —CH$_2$—, X and Y are each independently —O—, —NR$^6$— or —CH$_2$—, $R^4$ is —OR$^6$, —NR$^6$R$^7$ or —R$^6$, and $R^5$ is —NR$^6$R$^7$, —NR$^6$—NR$^6$R$^7$ or —N=NR$^6$, provided that $R^6$ is —C$_n$H$_{2n+1}$, $R^7$ is —C$_q$H$_{2q+1}$, and l, m, n and q are each independently 0 to 20), and the other is represented by M-C$_l$H$_{2l+1}$ (wherein M and l have the same meanings as mentioned above) or -(M-C$_l$H$_{2l}$)$_y$-C$_s$H$_{2s+1}$ (M and l have the same meanings as mentioned above, and y and s are each independently 1 to 20), provide that in one or more of $R^1$, $R^2$ and $R^3$, M is —O—].

Moreover, the silane compound (C) is desirable to be represented by the following general formula (II):

[Chem. 3]

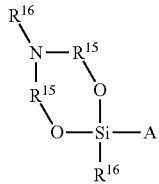

(II)

[In the formula (II), $A^1$ has the same meaning as mentioned above,
$R^{15}$ (two $R^{15}$ may be the same or different) is represented by —C$_l$H$_{2l}$— (l is 0 to 20), and
$R^{16}$ (two $R^{16}$ may be the same or different) is represented by -M-C$_r$H$_{2r+1}$ (wherein M has the same meaning as mentioned above, and r is 0 to 20) or -(M-C$_l$H$_{2l}$)$_y$C$_s$H$_{2s+1}$ (M and l have the same meanings as mentioned above, and y and s are each independently 1 to 20)].

Also, the silane compound (C) is desirable to contain a structure represented by the following general formula (III):

[Chem. 4]

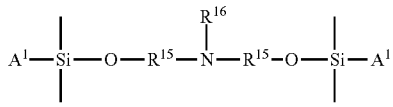

(III)

[In the formula (III), $A^1$, $R^{15}$ (two $R^{15}$ may be the same or different) and $R^{16}$ have the same meanings as mentioned above].

Moreover, the silane compound (C) is desirable to be a mixture of the silane compound represented by the general formula (II) and the silane compound containing the structure represented by the general formula (III).

Also, the above $A^1$ is desirable to contain at least one selected from the group consisting of hydrogen, haloalkyl group such as chloromethyl group, bromomethyl group, iodomethyl group, chloroethyl group, bromoethyl group, iodoethyl group, chloropropyl group, bromopropyl group and iodopropyl group, polysulfide group, thioester group, thiol group, dithiocarbonate group, dithioacetal group, hemithioacetal group, vinylthio group, α-thiocarbonyl group, β-thiocarbonyl group, S—CO—CH$_2$—O moiety, diketone group, and S—CH$_2$—Si moiety.

Moreover, the above $A^1$ is desirable to be represented by the following general formula (Ic), formula (Id) or formula (Ie):

[Chem. 5]

—R$^{12}$—A$^2$     (Ic)

$$—R^{12}—S_x—R^{12}—\underset{\underset{R^3}{|}}{\overset{\overset{R^1}{|}}{Si}}—A^2$$ (Id)

$$—R^{12}—S_x—R^{12}—\underset{\underset{R^{10}}{|}}{\overset{\overset{R^8—W}{|}}{Si}}—A^9$$ (Ie)

[In the formula (Ic), the formula (Id) and the formula (Ie), $R^{12}$ is —C$_t$H$_{2t}$— (t is 0 to 20),
in the formula (Ic), $A^2$ is —S—CO—R$^{13}$, —S—S—R$^{13}$, —S—CS—O—R$^{13}$, —R$^{14}$—Cl, —R$^{14}$—Br, —SH, —S—CO—O—R$^{13}$, or —S—CO—CO—R$^{13}$, provided that $R^{13}$ is —C$_r$H$_{2r+1}$, $R^{14}$ is —C$_r$H$_{2r}$—, and r and t are each independently 0 to 20,
in the formula (Id) and the formula (Ie), x is 1 to 10,
in the formula (Id), $R^1$, $R^2$ and $R^3$ have the same meanings as mentioned above, and
in the formula (Ie), W is represented by —NR$^6$—, —O— or —CR$^6$R$^{11}$— (wherein $R^6$ has the same meaning as mentioned above, $R^{11}$ is —R$^7$ or —C$_m$H$_{2m}$—R$^5$, provide that $R^7$ and $R^5$ have the same meanings as mentioned above, and m, n and q are each independently 0 to 20),
$R^8$ and $R^9$ are each independently represented by -M-C$_l$H$_{2l}$— (wherein M is —O— or —CH$_2$—, and l is 0 to 20), and
$R^{10}$ is represented by -M-C$_l$H$_{2l+1}$ or -M-C$_l$H$_{2l}$—R$^5$ (wherein M, l and $R^5$ have the same meanings as mentioned above) or -(M-C$_l$H$_{2l}$)$_y$C$_s$H$_{2s+1}$ (M and l have the same meanings as mentioned above, and y and s are each independently 1 to 20), provided that in one or more of $R^8$, $R^9$ and $R^{10}$, M is —O—].

The silane compound (C) is desirable to comprise at least one selected from the group consisting of 3-octanoylthio-propyl(monodimethylaminoethoxy)dimethoxysilane, 3-octanoylthio-propyl(didimethylaminoethoxy)monomethoxysilane, 3-octanoylthio-propyl tridimethylaminoethoxysilane, 3-octanoylthio-propyl(monodiethylaminoethoxy)dimethoxysilane, 3-octanoylthio-propyl(didiethylaminoethoxy) monomethoxysilane, 3-octanoylthio-propyl tridiethylaminoethoxysilane, 3-octanoylthio-propyl(dimethylaminoethoxy) methoxy methylsilane, 3-octanoylthio-propyl (dimethylaminoethoxy)dimethylsilane, 3-octanoylthio-propyl(didimethylaminoethoxy)monomethylsilane, 3-octanoylthio-propyl(diethylaminoethoxy)methoxy methylsilane, 3-octanoylthio-propyl(diethylaminoethoxy)dimethylsilane, 3-octanoylthio-propyl(didiethylaminoethoxy)monomethylsilane, 3-octanoylthio-propyl(methoxy)1,3-dioxa-6-methylaza-2-silacyclooctane, 3-octanoylthio-propyl(methoxy)1,3-dioxa-6-ethylaza-2-silacyclooctane, 3-octanoylthio-propyl(methoxy)1,3-dioxa-6-propylaza-2-silacyclooctane, 3-octanoylthio-propyl(methoxy)1,3-dioxa-6-butylaza-2-silacyclooctane, 3-octanoylthio-propyl(methoxy)1,3-dioxa-6-dodecylaza-2-silacyclooctane, 3-octanoylthio-propyl(methyl)1,3-dioxa-6-methylaza-2-silacyclooctane, 3-octanoylthio-propyl(methyl)1,3-dioxa-6-ethylaza-2-silacyclooctane, 3-octanoylthio-propyl(methyl)1,3-dioxa-6-propylaza-2-silacyclooctane, 3-octanoylthio-propyl(methyl)1,3-dioxa-6-butylaza-2-silacyclooctane, 3-octanoylthio-propyl(methyl)1,3-dioxa-6-dodecylaza-2-silacyclooctane, 3-ethylxanthogenate-propyl(monodimethylaminoethoxy)dimethoxysilane, 3-ethylxanthogenate-propyl(didimethylaminoethoxy)monomethoxysilane, 3-ethylxanthogenate-propyl tridimethylaminoethoxysilane, 3-ethylxanthogenate-propyl(monodiethylaminoethoxy)dimethoxysilane, 3-ethylxanthogenate-propyl(didiethylaminoethoxy)monomethoxysilane, 3-ethylxanthogenate-propyl tridiethylaminoethoxysilane, 3-ethylxanthogenate-propyl (dimethylaminoethoxy)methoxy methylsilane, 3-ethylxanthogenate-propyl (dimethylaminoethoxy)dimethylsilane, 3-ethylxanthogenate-propyl (didimethylaminoethoxy)monomethylsilane, 3-ethylxanthogenate-propyl (diethylaminoethoxy)methoxy methylsilane, 3-ethylxanthogenate-propyl (diethylaminoethoxy)dimethylsilane, 3-ethylxanthogenate-propyl (didiethylaminoethoxy)monomethylsilane, 3-ethylxanthogenate-propyl(methoxy)1,3-dioxa-6-methylaza-2-silacyclooctane, 3-ethylxanthogenate-propyl(methoxy)1,3-dioxa-6-ethylaza-2-silacyclooctane, 3-ethylxanthogenate-propyl(methoxy)1,3-dioxa-6-propylaza-2-silacyclooctane, 3-ethylxanthogenate-propyl(methoxy)1,3-dioxa-6-butylaza-2-silacyclooctane, 3-ethylxanthogenate-propyl(methoxy)1,3-dioxa-6-dodecylaza-2-silacyclooctane, 3-ethylxanthogenate-propyl(methyl)1,3-dioxa-6-methylaza-2-silacyclooctane, 3-ethylxanthogenate-propyl(methyl)1,3-dioxa-6-ethylaza-2-silacyclooctane, 3-ethylxanthogenate-propyl(methyl)1,3-dioxa-6-propylaza-2-silacyclooctane, 3-ethylxanthogenate-propyl(methyl)1,3-dioxa-6-butylaza-2-silacyclooctane, 3-ethylxanthogenate-propyl(methyl)1,3-dioxa-6-dodecylaza-2-silacyclooctane, 3-phenoxyethanoylthio-propyl (monodimethylaminoethoxy)dimethoxysilane, 3-phenoxyethanoylthio-propyl (didimethylaminoethoxy)monomethoxysilane, 3-phenoxyethanoylthio-propyl tridimethylaminoethoxysilane, 3-phenoxyethanoylthio-propyl (monodiethylaminoethoxy)dimethoxysilane, 3-phenoxyethanoylthio-propyl (didiethylaminoethoxy)monomethoxysilane, 3-phenoxyethanoylthio-propyl tridiethylaminoethoxysilane, 3-phenoxyethanoylthio-propyl(dimethylaminoethoxy)methoxy methylsilane, 3-phenoxyethanoylthio-propyl(dimethylaminoethoxy)dimethylsilane, 3-phenoxyethanoylthio-propyl(didimethylaminoethoxy)monomethylsilane, 3-phenoxyethanoylthio-propyl(diethylaminoethoxy)methoxy methylsilane, 3-phenoxyethanoylthio-propyl(diethylaminoethoxy)dimethylsilane, 3-phenoxyethanoylthio-propyl(didiethylaminoethoxy)monomethylsilane, 3-phenoxyethanoylthio-propyl (methoxy)1,3-dioxa-6-methylaza-2-silacyclooctane, 3-phenoxyethanoylthio-propyl(methoxy)1,3-dioxa-6-ethylaza-2-silacyclooctane, 3-phenoxyethanoylthio-propyl (methoxy)1,3-dioxa-6-propylaza-2-silacyclooctane, 3-phenoxyethanoylthio-propyl(methoxy)1,3-dioxa-6-butylaza-2-silacyclooctane, 3-phenoxyethanoylthio-propyl(methoxy)1,3-dioxa-6-dodecylaza-2-silacyclooctane, 3-phenoxyethanoylthio-propyl(methyl)1,3-dioxa-6-methylaza-2-silacyclooctane, 3-phenoxyethanoylthio-propyl(methyl)1,3-dioxa-6-ethylaza-2-silacyclooctane, 3-phenoxyethanoylthio-propyl(methyl)1,3-dioxa-6-propylaza-2-silacyclooctane, 3-phenoxyethanoylthio-propyl(methyl)1,3-dioxa-6-butylaza-2-silacyclooctane, 3-phenoxyethanoylthio-propyl(methyl)1,3-dioxa-6-dodecylaza-2-silacyclooctane, 3-ethyloxalylthio-propyl(monodimethylaminoethoxy)dimethoxysilane, 3-ethyloxalylthio-propyl(didimethylaminoethoxy)monomethoxysilane, 3-ethyloxalylthio-propyl tridimethylaminoethoxysilane, 3-ethyloxalylthio-propyl (monodiethylaminoethoxy)dimethoxysilane, 3-ethyloxalylthio-propyl (didiethylaminoethoxy)monomethoxysilane, 3-ethyloxalylthio-propyl tridiethylaminoethoxysilane, 3-ethyloxalylthio-propyl (dimethylaminoethoxy)methoxy methylsilane, 3-ethyloxalylthio-propyl(dimethylaminoethoxy)dimethylsilane, 3-ethyloxalylthio-propyl(didimethylaminoethoxy)monomethylsilane, 3-ethyloxalylthio-propyl(diethylaminoethoxy)methoxy methylsilane, 3-ethyloxalylthio-propyl (diethylaminoethoxy)dimethylsilane, 3-ethyloxalylthio-propyl(didiethylaminoethoxy)monomethylsilane, 3-ethyloxalylthio-propyl(methoxy)1,3-dioxa-6-methylaza-2-silacyclooctane, 3-ethyloxalylthio-propyl(methoxy)1,3-dioxa-6-ethylaza-2-silacyclooctane, 3-ethyloxalylthio-propyl(methoxy)1,3-dioxa-6-propylaza-2-silacyclooctane, 3-ethyloxalylthio-propyl(methoxy)1,3-dioxa-6-butylaza-2-silacyclooctane, 3-ethyloxalylthio-propyl(methoxy)1,3-dioxa-6-dodecylaza-2-silcyclooctane, 3-ethyloxalylthio-propyl(methyl)1,3-dioxa-6-methylaza-2-silacyclooctane, 3-ethyloxalylthio-propyl(methyl)1,3-dioxa-6-ethylaza-2-silacyclooctane, 3-ethyloxalylthio-propyl(methyl)1,3-dioxa-6-propylaza-2-silacyclooctane, 3-ethyloxalylthio-propyl (methyl)1,3-dioxa-6-butylaza-2-silacyclooctane, 3-ethyloxalylthio-propyl(methyl)1,3-dioxa-6-dodecylaza-2-silacyclooctane, bis(3-(monodimethylaminoethoxy)dimethoxysilyl-propyl)disulfide, bis(3-(didimethylaminoethoxy)monomethoxysilyl-propyl)disulfide, bis(3-(tridimethylaminoethoxy)silyl-propyl)disulfide, bis(3-(monodiethylaminoethoxy)dimethoxysilyl-propyl)disulfide, bis(3-(didiethylaminoethoxy)monomethoxysilyl-propyl) disulfide, bis(3-(tridiethylaminoethoxy)silyl-propyl)disulfide, bis(3-(dimethylaminoethoxy)methoxymethylsilyl-propyl)disulfide, bis(3-(dimethylaminoethoxy)dimethylsilyl-propyl)disulfide, bis(3-(didimethylaminoethoxy)monomethylsilyl-propyl)disulfide, bis(3-(diethylaminoethoxy)methoxymethylsilyl-propyl)disulfide, bis(3-(diethylaminoethoxy)dimethylsilyl-propyl)disulfide, bis(3-(didiethylaminoethoxy)monomethylsilyl-propyl)disulfide, bis(3-(methoxy)1,3-dioxa-6-methylaza-2-silacyclooctyl-propyl)disulfide, bis(3-(methoxy)1,3-dioxa-6-ethylaza-2-silacyclooctyl-propyl)disulfide, bis(3-(methoxy)1,3-dioxa-6-propylaza-2-silacyclooctyl-propyl)disulfide, bis(3-(methoxy)1,3-dioxa-6-butylaza-2-silacyclooctyl-propyl) disulfide, bis(3-(methoxy)1,3-dioxa-6-dodecylaza-2-silacyclooctyl-propyl)disulfide, bis(3-(methyl)1,3-dioxa-6-methylaza-2-silacyclooctyl-propyl)disulfide, bis(3-(methyl)1,3-dioxa-6-ethylaza-2-silacyclooctyl-propyl)disulfide, bis(3-(methyl)1,3-dioxa-6-propylaza-2-silacyclooctyl-propyl) disulfide, bis(3-(methyl)1,3-dioxa-6-butylaza-2-silacyclooctyl-propyl)disulfide, bis(3-(methyl)1,3-dioxa-6-dodecylaza-2-silacyclooctyl-propyl)disulfide, bis(3-(monodimethylaminoethoxy)dimethoxysilyl-propyl) tetrasulfide, bis(3-(didimethylaminoethoxy)monomethoxysilyl-propyl)tetrasulfide, bis(3-(tridimethylaminoethoxy)silyl-propyl)tetrasulfide, bis(3-

(monodiethylaminoethoxy)dimethoxysilyl-propyl)tetrasulfide, bis(3-(didiethylaminoethoxy)monomethoxysilyl-propyl)tetrasulfide, bis(3-(tridiethylaminoethoxy)silyl-propyl)tetrasulfide, bis(3-(dimethylaminoethoxy)methoxymethylsilyl-propyl)tetrasulfide, bis(3-(dimethylaminoethoxy)dimethylsilyl-propyl)tetrasulfide, bis(3-(didimethylaminoethoxy)monomethylsilyl-propyl)tetrasulfide, bis(3-(diethylaminoethoxy)methoxymethylsilyl-propyl)tetrasulfide, bis(3-(diethylaminoethoxy)dimethylsilyl-propyl)tetrasulfide, bis(3-(didiethylaminoethoxy)monomethylsilyl-propyl)tetrasulfide, bis(3-(methoxy)1,3-dioxa-6-methylaza-2-silacyclooctyl-propyl)tetrasulfide, bis(3-(methoxy)1,3-dioxa-6-ethylaza-2-silacyclooctyl-propyl)tetrasulfide, bis(3-(methoxy)1,3-dioxa-6-propylaza-2-silacyclooctyl-propyl)tetrasulfide, bis(3-(methoxy)1,3-dioxa-6-butylaza-2-silacyclooctyl-propyl)tetrasulfide, bis(3-(methoxy)1,3-dioxa-6-dodecylaza-2-silacyclooctyl-propyl)tetrasulfide, bis(3-(methyl)1,3-dioxa-6-methylaza-2-silacyclooctyl-propyl)tetrasulfide, bis(3-(methyl)1,3-dioxa-6-ethylaza-2-silacyclooctyl-propyl)tetrasulfide, bis(3-(methyl)1,3-dioxa-6-propylaza-2-silacyclooctyl-propyl)tetrasulfide, bis(3-(methyl)1,3-dioxa-6-butylaza-2-silacyclooctyl-propyl)tetrasulfide, bis(3-(methyl)1,3-dioxa-6-dodecylaza-2-silacyclooctyl-propyl)tetrasulfide, tri(dimethylaminoethoxy)silane, tri(diethylaminoethoxy)silane, tri(dibutylaminoethoxy)silane, di(dimethylaminoethoxy)methylsilane, di(dimethylaminoethoxy)methoxysilane, di(dimethylaminoethoxy)ethoxysilane, (dimethylaminoethoxy)diethoxylsilane, (dimethylaminoethoxy)methyl ethoxysilane, 1,3-dioxa-6-methylaza-2-ethoxysila-cyclooctane, 1,3-dioxa-6-methylaza-2-methylsila-cyclooctane, 1,3-dioxa-6-butylaza-2-ethoxysila-cyclooctane, 1,3-dioxa-6-butylaza-2-methylsila-cyclooctane, tri(dimethylaminoethoxy)silylpropyl chloride, tri(diethylaminoethoxy)silylpropyl chloride, tri(dibutylaminoethoxy)silylpropyl chloride, di(dimethylaminoethoxy)methylsilylpropyl chloride, di(dimethylaminoethoxy)methoxysilylpropyl chloride, di(dimethylaminoethoxy)ethoxysilylpropyl chloride, (dimethylaminoethoxy)diethoxysilylpropyl chloride, (dimethyaminoethoxy)methylethoxysilylpropyl chloride, 1,3-dioxa-6-methylaza-2-ethoxysila-cyclooctylpropyl chloride, 1,3-dioxa-6-methylaza-2-methylsila-cyclooctylpropyl chloride, 1,3-dioxa-6-butylaza-2-ethoxysila-cyclooctylpropyl chloride, and 1,3-dioxa-6-butylaza-2-methylsila-cyclooctyl-propyl chloride.

Effect of the Invention

According to the invention, by reacting the silane compound (A) with the compound (B) which has the hydroxyl group and further contains the atom having the unshared electron pair other than the oxygen atom derived from the hydroxyl group, in the presence of the metal-containing catalyst (m), it is possible to provide the silane compound (C) which has the alkoxyl group containing the atom having the unshared electron pair other than the oxygen atom derived from the hydroxyl group, shortening the time required for the production process, while inhibiting a side reaction.

BEST MODE FOR CARRYING OUT THE INVENTION

The invention will be described in details below. The process for producing the silane coupling agent of the invention is characterized by comprising the step of reacting the silane compound (A) with the compound (B) which has the hydroxyl group and further contains the atom having the unshared electron pair other than the oxygen atom derived from the hydroxyl group, in the presence of the metal-containing catalyst (m) to obtain the silane compound (C) which has the alkoxyl group containing the atom having the unshared electron pair other than the oxygen atom derived from the hydroxyl group. According to the invention, since the objective silane compound (C) can be obtained in a shorter time through the reaction in the presence of the metal-containing catalyst (m), it becomes possible to reduce the production cost and the production time of the silane coupling agent. Also, the silane compound (C) has the alkoxyl group containing the atom having another unshared electron pair other than the oxygen atom derived from the hydroxyl group possessed by the compound (B). Therefore, by selecting the kind of atoms having the unshared electron pair, and designing the structure of the alkoxyl group, it is possible to efficiently develop a novel silane coupling agent.

<<Silane Compound (A)>>

The silane compound (A) used in the process for producing the silane coupling agent of the invention is not particularly limited as long as it is a silane compound which can react with a hydroxyl group, but preferably includes halogenated silane, hydrosilane, alkoxysilane (i.e., a silane compound containing an alkoxyl group), and the like. More specifically, a silane compound represented by the following general formula (IV):

[Chem. 6]

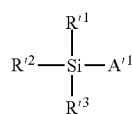

[Chem. 6]

[In the formula (IV), $A'^1$ is a monovalent group, at least one of $R'^1$, $R'^2$ and $R'^3$ is represented by $-O-C_lH_{2l+1}$ (wherein l is 0 to 20) or $-X$ (wherein X is F, Cl, Br or I), and the other is represented by $-(M-C_lH_{2l})_yC_sH_{2s+1}$ (wherein M is $-O-$ or $-CH_2-$, l and y are each independently 0 to 20, and s is 1 to 20)] is preferable.

In the above formula (IV), since l is 0 to 20, $-C_lH_{2l+1}$ is hydrogen or an alkyl group with 1 to 20 carbons, and since s is 1 to 20, $-C_sH_{2s+1}$ is an alkyl group with 1 to 20 carbons. Here, the alkyl groups with 1 to 20 carbons include methyl group, ethyl group, propyl group, butyl group, pentyl group, hexyl group, heptyl group, octyl group, decyl group, dodecyl group, tridecyl group, tetradecyl group, pentadecyl group, hexadecyl group, heptadecyl group, stearyl group and the like, and the alkyl groups may be linear or branched. Also, since l is 0 to 20, $-C_lH_{2l}$ is a single bond or an alkylene group with 1 to 20 carbons. Here, the alkylene group with 1 to 20 carbons includes methylene group, ethylene group, trimethylene group, propylene group and the like, and the alkylene groups may be linear or branched.

In the above formula (IV), $A'^1$ is not particularly limited as long as it is a monovalent group, but preferable to be a group containing hydrogen, haloalkyl group, polysulfide group, thioester group, thiol group, dithiocarbonate group, dithioacetal group, hemithioacetal group, vinylthio group, α-thiocarbonyl group, β-thiocarbonyl group, $S-CO-CH_2-O$ moiety, diketone group, $S-CH_2-Si$ moiety and the like, from the perspective of adding to a rubber composition compounded with an inorganic filler to improve the coupling efficiency. Also, from the similar perspective, the above A'¹ may be a group represented by the following formula (IVa) or formula (IVb):

[Chem. 7]

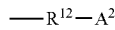   (IVa)

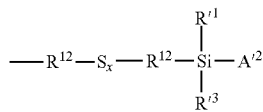   (IVb)

[A² in the formula (IVa) is —S—CO—R¹³, —S—S—R¹³, —S—CS—O—R¹³, —R¹⁴—Cl, —R¹⁴—Br, —SH, —S—CO—O—R¹³, or —S—CO—CO—R¹³, provided that R¹³ is —$C_rH_{2r+1}$, R¹⁴ is —$C_tH_{2t}$—, and r and t are each independently 0 to 20, R¹² in the formula (IVa) and the formula (IVb) is —$C_tH_{2t}$— (wherein t is 0 to 20), at least one of R'¹, R'² and R'³ in the formula (IVb) is represented by -M-$C_lH_{2l+1}$ (wherein M is —O— or —CH₂—, and l is 0 to 20), and the other is represented by -(M-$C_lH_{2l}$)$_y$$C_sH_{2s+1}$ (wherein M and l have the same meanings as mentioned above, y and s are each independently 1 to 20), provided that in one or more of R'¹, R'² and R'³, M is —O—, and x in the formula (IVb) is 1 to 10].

In the above formula (IVa), since r is 0 to 20, —$C_rH_{2r+1}$ is hydrogen or an alkyl group with 1 to 20 carbons, and in the above formula (IVa) and the formula (IVb), since t is 0 to 20, —$C_tH_{2t}$— is a single bond or an alkylene group with 1 to 20 carbons. In addition, the alkyl group with 1 to 20 carbons and the alkylene group with 1 to 20 carbons are as described above. Moreover, x in the formula (IVb) is 1 to 10, preferably 2 to 4. In addition, $C_lH_{2l+1}$, —$C_sH_{2s+1}$ and —$C_tH_{2t}$— are as described above.

Specific examples of the silane compound (A) include trichlorosilane, methyl dichlorosilane, trichlorosilylpropyl chloride, methyldichlorosilylpropyl chloride, trimethoxysilane, triethoxysilane, methyl dimethoxysilane, methyl diethoxysilane, octyl(monomethyl)dimethoxysilane, 3-chloro-propyl(monomethyl)dimethoxysilane, 3-mercapto-propyl(monomethyl)dimethoxysilane, 3-octanoylthio-propyl(monomethyl)dimethoxysilane, 3-ethylxanthogenate-propyl(monomethyl)dimethoxysilane, 3-phenoxyethanoylthio-propyl(monomethyl)dimethoxysilane, 3-ethyloxalylthio-propyl(monomethyl)dimethoxysilane, bis(3-(monomethyl)dimethoxysilyl-propyl)disulfide, bis(3-(monomethyl)dimethoxysilyl-propyl)tetrasulfide and the like.

<<Compound B>>

In the process for producing the silane coupling agent of the invention, the compound (B) to be reacted with the above silane compound (A) is required to have the hydroxyl group, and further contain the atom having the unshared electron pair other than the oxygen atom derived from the hydroxyl group. Here, while the reaction with the silane compound (A) is achieved by the hydroxyl group, it is assumed that in the invention, since the compound (B) further contains the atom having the unshared electron pair other than the oxygen atom derived from the hydroxyl group, a side reaction can be inhibited through a different process from the conventional reaction pathway.

Moreover, as the atom having the unshared electron pair other than the oxygen atom derived from the hydroxyl group, a nitrogen atom or an oxygen atom is preferable, and the nitrogen atom is particularly preferable, from the perspective of adding to the rubber composition compounded with the inorganic filler to improve the coupling efficiency.

For example, the above compound (B) includes a compound containing an amino group, imino group, substituted amino group, substituted imino group and the like, and a compound containing an aminoalkoxyl group as an alkoxyl group containing the nitrogen functional group, and specifically and preferably includes dimethylaminoethanol, diethylaminoethanol, dibutylaminoethanol, N-methyldiethanolamine, N-butyldiethanolamine, N-lauryldiethanolamine and the like.

In the process for producing the silane coupling agent of the invention, the amount of the compound (B) used is preferable to be within a range of 0.9 to 1.1 molar equivalent, and more preferable to be 1 molar equivalent per mole of silyl group of the silane compound as raw material. When the amount of the compound (B) used is less than 0.9 molar equivalent per mole of silyl group of the silane compound as raw material, the reaction is not completed, while when it is more than 1.1 molar equivalent, impurities are liable to be generated.

<<Metal-Containing Catalyst (m)>>

The process for producing the silane coupling agent of the invention can use Groups 1 to 12, and Groups 13 to 14 of the periodic table (it will be shown in the IUPAC format. In addition, within the bracket will be shown in the previous CAS format.) as the metal-containing catalyst (m), and for example, a metal compound of the lanthanide group and the like can also be used. Moreover, as the metal-containing catalyst (m), a transition metal compound can be used.

The metal-containing catalyst (m) may be a metal compound, for example metal chloride, metal oxide, metal oxychloride, metal sulfide, metal sulphochloride, metal alcolate (metal alkoxide), metal thiolate, metal oxyalcolate (metal oxyalkoxide), metal amide, metal imide or a transition metal compound having a multiple bonded ligand. Here, for zinc of Group 12, the definition of being included in transition metals is adopted, and boron of Group 13 (Main Group 3), silicon and germanium of Group 14 (Main Group 4) are classified into semimetals, which may not be seen as metals scholarly but are included in one of metal elements constituting the metal-containing catalyst (m) due to its catalytic activity in the invention.

For example, as the metal compound, halide, sulfide, amide, thiolate or alcolate (alkoxide) of Group 1

($M^+$=Li, Na, K, Rb, Cs:

$M^+$(OMe), $M^+$(OEt), $M^+$($OC_3H_7$), $M^+$($OC_4H_9$), wherein Me=methyl group, Et=ethyl group, cp=cyclopentadienyl anion ligand), halide, sulfide, amide, thiolate or alcolate (alkoxide) of Group 2 ($M^{2+}$=Be, Mg, Ca, Sr, Ba:

$M^{2+}$$(OMe)_2$, $M^{2+}$$(OEt)_2$, $M^{2+}$$(OC_3H_7)_2$, $M^{2+}$$(OC_4H_9)_2$), halide, oxide, sulfide, imide, alcolate (alkoxide), amide, thiolate and combination of the above substituent classes having a ligand multiple bonded on a compound of Group 3 (Subgroup 3: part of rare earth)

($M^{3+}$=Sc, Y, La:

$M^{3+}$$(OMe)_3$, $M^{3+}$$(OEt)_3$, $M^{3+}$$(OC_3H_7)_3$, $M^{3+}$$(OC_4H_9)_3$, cp$M^{3+}$$(Cl)_2$, cp$M^{3+}$$(OMe)_2$, cp$M^{3+}$$(OEt)_2$, cp$M^{3+}$$(NMe_2)_2$), halide, oxide, sulfide, imide, alcolate (alkoxide), amide, thiolate and combination of the above substituent classes having a ligand multiple bonded on a compound of Group 3

(Lanthanide Group: part of rare earth, atomic numbers 58 to 71 in the periodic table of the elements), halide, oxide, sulfide, imide, alcolate (alkoxide), amide, thiolate and combination of the above substituent classes having a ligand multiple bonded on a compound of Group 4 (Subgroup 4)

($M^{4+}$=Ti, Zr, Hf:
$M^{4+}(F)_4$, $M^{4+}(Cl)_4$, $M^{4+}(Br)_4$, $M^{4+}(I)_4$, $M^{4+}(OMe)_4$, $M^{4+}(OEt)_4$, $M^{4+}(OC_3H_7)_4$, $M^{4+}(OC_4H_9)_4$, $cp_2Ti(Cl)_2$, $cp_2Zr(Cl)_2$, $cp_2Hf(Cl)_2$, $cp_2Ti(OMe)_2$, $cp_2Zr(OMe)_2$, $cp_2Hf(OMe)_2$, $cpTi(Cl)_3$, $cpZr(Cl)_3$, $cpHf(Cl)_3$, $cpTi(OMe)_3$, $cpZr(OMe)_3$, $cpHf(OMe)_3$, $M^{4+}(NMe_2)_4$, $M^{4+}(NEt_2)_4$, $M^{4+}(NHC_4H_9)_4$), halide, oxide, sulfide, imide, alcolate (alkoxide), amide, thiolate and combination of the above substituent classes having a ligand multiple bonded on a compound of Group 5 (Subgroup 5)

($M^{5+}$, $M^{4+}$ or $M^{3+}$=V, Nb, Ta:
$M^{5+}(OMe)_5$, $M^{5+}(OEt)_5$, $M^{5+}(OC_3H_7)_5$, $M^{5+}(OC_4H_9)_5$, $M^{3+}O(OMe)_3$, $M^{3+}O(OEt)_3$, $M^{3+}O(OC_3H_7)_3$, $M^{3+}O(OC_4H_9)_3$, $cpV(OMe)_4$, $cpNb(OMe)_4$, $cpTa(OMe)_4$, $cpV(OMe)_2$, $cpNb(OMe)_2$, $cpTa(OMe)_2$), halide, oxide, sulfide, imide, alcolate (alkoxide), amide, thiolate and combination of the above substituent classes having a ligand multiple bonded on a compound of Group 6 (Subgroup 6)

($M^{6+}$, $M^{5+}$ or $M^{4+}$=Cr, Mo, W:
$M^{6+}(OMe)_6$, $M^{6+}(OEt)_6$, $M^{6+}(OC_3H_7)_6$, $M^{6+}(OC_4H_9)_6$, $M^{6+}O(OMe)_4$, $M^{6+}O(OEt)_4$, $M^{6+}O(OC_3H_7)_4$, $M^{6+}O(OC_4H_9)_4$, $M^{6+}O_2(OMe)_2$, $M^{6+}O_2(OEt)_2$, $M^{6+}O_2(OC_3H_7)_2$, $M^{6+}O_2(OC_4H_9)_2$, $M^{6+}O_2(OSiMe_3)_2$), halide, oxide, sulfide, imide, alcolate (alkoxide), amide, thiolate and combination of the above substituent classes having a ligand multiple bonded on a compound of Group 7 (Subgroup 7)

($M^{7+}$, $M^{6+}$, $M^{5+}$ or $M^{4+}$=Mn, Re:
$M^{7+}O(OMe)_5$, $M^{7+}O(OEt)_5$, $M^{7+}O(OC_3H_7)_5$, $M^{7+}O(OC_4H_9)_5$, $M^{7+}O_2(OMe)_3$, $M^{7+}O_2(OEt)_3$, $M^{7+}O_2(OC_3H_7)_3$, $M^{7+}O_2(OC_4H_9)_3$, $M^{7+}O_2(OSiMe_3)_3$, $M^{7+}O_3(OSiMe_3)$, $M^{7+}O_3(Me)$), halide, sulfide, amide, thiolate or alcolate (alkoxide) of Groups 8 to 12

($M^{2+}$ or $M^{3+}$=Fe, Co, Ni:
$M^{2+}(OMe)_2$, $M^{2+}(OEt)_2$, $M^{2+}(OC_3H_7)_2$, $M^{2+}(OC_4H_9)_2$, $M^{3+}(OMe)_3$, $M^{3+}(OEt)_3$, $M^{3+}(OC_3H_7)_3$, $M^3(OC_4H_9)_3$), ($M^+$ or $M^{2+}$=Cu:
$M^+(OMe)$, $M^+(OEt)$, $M^+(OC_3H_7)$, $M^+(OC_4H_9)$, $M^{2+}(OMe)_2$, $M^{2+}(OEt)_2$, $M^{2+}(OC_3H_7)_2$, $M^{2+}(OC_4H_9)_2$, $M^{3+}(OMe)_3$, $M^{3+}(OEt)_3$, $M^{3+}(OC_3H_7)_3$, $M^{3+}(OC_4H_9)_3$), ($M^{2+}$=Zn:
$M^{2+}(OMe)_2$, $M^{2+}(OEt)_2$, $M^{2+}(OC_3H_7)_2$, $M^{2+}(OC_4H_9)_2$), halide, amide or alcolate (alkoxide) of Group 13 (Main Group 3)

($M^{3+}$=B, Al, Ga, In, Tl:
$M^{3+}(OMe)_3$, $M^{3+}(OEt)_3$, $M^{3+}(OC_3H_7)_3$, $M^{3+}(OC_4H_9)_3$), halide, sulfide, amide, thiolate or alcolate (alkoxide) of Group 14 (Main Group 4)

($M^{4+}$=Si, Ge, Sn, Pb:
$M^{4+}(OMe)_4$, $M^{4+}(OEt)_4$, $M^{4+}(OC_3H_7)_4$, $M^{4+}(OC_4H_9)_4$;
$M^{2+}$+Sn, Pb:
$M^{2+}(OMe)_2$, $M^{2+}(OEt)_2$, $M^{2+}(OC_3H_7)_2$, $M^{2+}(OC_4H_9)_2$), tin dilaurate, tin diacetate, $Sn(OC_4H_9)_2$ can be used.

The above metal compounds, particularly transition metal compounds may have free coordination sites on metal.

Also, as the metal-containing catalyst (m), a metal compound for forming a hydrolysable metal compound by the addition of water can also be used.

Moreover, as the metal-containing catalyst (m), a metal alkoxide is preferable. Furthermore, the metal contained in the metal alkoxide is preferable to be at least one selected from the group consisting of lithium, sodium, potassium, rubidium, cesium, beryllium, magnesium, calcium, strontium, barium, boron, aluminum, gallium, indium, yttrium, titanium, zirconium, niobium, chromium, manganese, iron, cobalt, nickel, copper and zinc, and the metal-containing catalyst (m) is more preferable to be an aluminum alkoxide.

In one embodiment of the invention, for example, as the metal-containing catalyst (m), the aluminum alkoxide can preferably be used, and particularly aluminum tri-n-butoxide, aluminum trimethoxide, aluminum triethoxide, aluminum tri-n-propoxide, aluminum tri-t-butoxide or aluminum triisopropoxide can be used as the metal-containing catalyst (m).

The amount of the metal-containing catalyst (m) used is arbitrarily selected depending on the metal contained, the silane compound (A) to be reacted and the like, but is preferable to be within a range of 0.1 to 100 mmol per 1 mol of the silane compound (A).

<<Solvent>>

The process for producing the silane coupling agent of the invention can apply with or without a solvent. The weight of the solvent used based on the total weight of raw materials is preferable to be within a range of 0 to 10 times, and particularly preferable to be 0 to 4 times.

<<Reaction Temperature>>

In the process for producing the silane coupling agent of the invention, the reaction in the presence of the metal-containing catalyst (m) is preferable to have the reaction temperature within a range of 50 to 200° C., it is more preferable to be within a range of 90 to 170° C., and moreover, particularly preferable to be within a range of 130 to 170° C. When the reaction temperature is within the range specified above, the reaction rate can be accelerated, and the side reaction can be substantially inhibited. Also, when the reaction temperature is less than 50° C., the reaction may not progress, while when it is more than 200° C., impurities are liable to be generated.

<<Reaction Time>>

In the process for the production of silane coupling agents of the invention, the reaction in the presence of the metal-containing catalyst (m) is preferable to have the reaction time within a range of 0.5 to 6 hours, and moreover, it is further preferable to be 1 to 6 hours. When the reaction time is within the range specified above, the yield of the silane compound (C) as a product can be sufficiently ensured, while inhibiting the side reaction. Also, when the reaction time in the absence of a solvent is less than 0.5 hour, the reaction may not be completed, while when it is more than 6 hours, impurities are liable to be generated as well as unecomonicality due to the lapse of time after the reaction has been completed.

<<Silane Compound (C)>>

The silane compound (C) obtained by the process for producing the silane coupling agent of the invention has the alkoxyl group containing the atom having the unshared electron pair other than the oxygen atom derived from the hydroxyl group possessed by the compound (B), and here, as the atom having the unshared electron pair, a nitrogen atom or an oxygen atom is preferable, and the nitrogen atom is particularly preferable, from the perspective of adding to the rubber composition compounded with the inorganic filler to improve the coupling efficiency. Also, more specifically, as the silane compound (C), the silane compounds represented by the above formula (I) and the above formula (II), and the silane compound having the structure represented by the above formula (III) are preferable.

<<Silane Compound Represented by the Formula (I)>>

In the above formula (I), at least one of $R^1$, $R^2$ and $R^3$ is represented by the above general formula (Ia) or formula (Ib), and the other is represented by -M-$C_lH_{2l+1}$ (wherein M is —O— or —$CH_2$—, and l is 0 to 20, preferable to be within a range of 0 to 10) or -(M-$C_lH_{2l}$)$_y$$C_sH_{2s+1}$ (M and l have the same meanings as mentioned above, and y and s are each independently 1 to 20). In this regard, however, in one or more of $R^1$, $R^2$ and $R^3$, M is —O—. In addition, since l is 0 to 20, —$C_lH_{2l+1}$ is hydrogen or an alkyl group with 1 to 20 carbons. Also, since s is 1 to 20, —$C_sH_{2s+1}$ is an alkyl group with 1 to 20 carbons. Here, the alkyl groups with 1 to 20 carbons include methyl group, ethyl group, propyl group, butyl group, pentyl group, hexyl group, heptyl group, octyl group, decyl group, dodecyl group, tridecyl group, tetradecyl group, pentadecyl group, hexadecyl group, heptadecyl group, stearyl group and the like, and the alkyl groups may be linear or branched. Also, since l is 0 to 20, —$C_lH_{2l}$— is a single bond or an alkylene group with 1 to 20 carbons. Here, the alkylene group with 1 to 20 carbons includes methylene group, ethylene group, trimethylene group, propylene group and the like, and the alkylene groups may be linear or branched.

In the above formulae (Ia) and (Ib), M is —O— or —$CH_2$—, and l is 0 to 20, preferable to be within a range of 0 to 10. Also, in the above formula (Ia), m is 0 to 20, preferable to be within a range of 0 to 10. In addition, since m is 0 to 20, —$C_mH_{2m+1}$ is hydrogen or an alkyl group with 1 to 20 carbons. The alkyl group with 1 to 20 carbons is as described above.

In the above formula (Ia), X and Y are each independently —O—, —$NR^6$— or —$CH_2$—. Here, $R^6$ is —$C_nH_{2n+1}$, and n is 0 to 20, preferable to be within a range of 0 to 10. In addition, since n is 0 to 20, —$C_nH_{2n+1}$ is hydrogen or an alkyl group with 1 to 20 carbons. Also, $R^4$ is —$OR^6$, —$NR^6R^7$ or —$R^6$. Here, $R^6$ is —$C_nH_{2n+1}$, $R^7$ is —$C_qH_{2q+1}$, and n and q are each independently 0 to 20, preferable to be within a range of 0 to 10. In addition, —$C_nH_{2n+1}$ is as described above, and since q is 0 to 20, —$C_qH_{2q+1}$ is hydrogen or an alkyl group with 1 to 20 carbons. Moreover, the alkyl group with 1 to 20 carbons is as descried above.

In the above formula (Ib), $R^5$ is —$NR^6R^7$, —$NR^6$—$NR^6R^7$ or —N=$NR_6$. Here, $R^6$ is —$C_nH_{2n+1}$, $R^7$ is —$C_qH_{2q+1}$, and n and q are each independently 0 to 20, preferable to be within a range of 0 to 10. In addition, —$C_nH_{2n+1}$ and —$C_qH_{2q+1}$ are as described above.

Moreover, in the above formula (I), $A^1$ is a monovalent group, and preferable to contain hydrogen, haloalkyl group such as chloromethyl group, bromomethyl group, iodomethyl group, chloroethyl group, bromoethyl group, iodoethyl group, chloropropyl group, bromopropyl group and iodopropyl group, polysulfide group, thioester group, thiol group, dithiocarbonate group, dithioacetal group, hemithioacetal group, vinylthio group, α-thiocarbonyl group, β-thiocarbonyl group, S—CO—$CH_2$—O moiety, diketone group, S—$CH_2$—Si moiety and the like, from the perspective of adding to the rubber composition compounded with the inorganic filler to improve the coupling efficiency. Also, from the similar perspective, the above $A^1$ is preferable to be represented by the above general formula (Ic), formula (Id) or formula (Ie).

In the formula (Ic), r is 0 to 20, preferable to be within a range of 0 to 10, and in the formula (Ic), the formula (Id) and the formula (Ie), t is 0 to 20, preferable to be within a range of 0 to 10. Moreover, since r is 0 to 20, —$C_rH_{2r+1}$ is hydrogen or an alkyl group with 1 to 20 carbons, and since t is 0 to 20, —$C_tH_{2t}$— is a single bond or an alkylene group with 1 to 20 carbons. The alkyl group with 1 to 20 carbons and the alkylene group with 1 to 20 carbons are as described above. Furthermore, $R^1$, $R^2$ and $R^3$ in the formula (Id) have the same meanings as mentioned above, and also W in the formula (Ie) is represented by —$NR^6$—, —O— or —$CR^6R^{11}$—, wherein $R^{11}$ is —$R^7$ or —$C_mH_{2m}$—$R^5$, provided that $R^5$ is —$NR^6R^7$, —$NR^6$—$NR^6R^7$, or —N=$NR^6$, $R^6$ is —$C_nH_{2n+1}$, $R^7$ is —$C_qH_{2q+1}$, and m, n and q are each independently 0 to 20, preferable to be within a range of 0 to 10. In addition, since m is 0 to 20, —$C_mH_{2m}$— is a single bond or an alkylene group with 1 to 20 carbons. Here, the alkylene group with 1 to 20 carbons includes methylene group, ethylene group, trimethylene group, propylene groups and the like, and the alkylene group may be linear or branched. Also, since n and q are 0 to 20, —$C_nH_{2n+1}$ and —$C_qH_{2q+1}$ are hydrogen or an alkyl group with 1 to 20 carbons. Here, the alkyl group with 1 to 20 carbons includes methyl group, ethyl group, propyl group, butyl group, pentyl group, hexyl group, heptyl group, octyl group, decyl group, dodecyl group, tridecyl group, tetradecyl group, pentadecyl group, hexadecyl group, heptadecyl group, stearyl group and the like, and the alkyl group may be linear or branched.

In the above formula (Ie), $R^8$ and $R^9$ are each independently represented by -M-$C_tH_{2t}$—, and $R^{10}$ is represented by -M-$C_lH_{2l+1}$, -M-$C_lH_{2l}$—$R^5$ or -(M-$C_lH_{2l}$)$_y$$C_sH_{2s+1}$, wherein M is —O— or —$CH_2$—, $R^5$ is —$NR^6R^7$, —$NR^6$—$NR^6R^7$, or —N=$NR^6$, $R^6$ is —$C_nH_{2n+1}$, $R^7$ is —$C_qH_{2q+1}$, l, n and q are each independently 0 to 20, preferable to be within a range of 0 to 10, and y and s are each independently 1 to 20. In this regard, however, in one or more of $R^8$, $R^9$ and $R^{10}$, M is —O—. In addition, since l is 0 to 20, —$C_lH_{2l}$— is a single bond or an alkylene group with 1 to 20 carbons, and here, the alkylene group with 1 to 20 carbons is as described above. Moreover, since l is 0 to 20, —$C_lH_{2l+1}$ is hydrogen or an alkyl group with 1 to 20 carbons. Furthermore, since s is 1 to 20, —$C_sH_{2s+1}$ is an alkyl group with 1 to 20 carbons. Here, the alkyl groups with 1 to 20 carbons are as described above. In addition, —$C_nH_{2n+1}$ and —$C_qH_{2q+1}$ are as described above. Also moreover, x in the formula (Id) and the formula (Ie) is 1 to 10, preferably 2 to 4.

<<Silane Compound Represented by the Formula (II)>>

In the above formula (II), $A^1$ has the same meaning as mentioned above, $R^{15}$ is represented by —$C_lH_{2l}$— (l is 0 to 20), $R^{16}$ is represented by -M-$C_rH_{2r+1}$ (wherein M has the same meaning as mentioned above, and r is 0 to 20) or -(M-$C_lH_{2l}$)$_y$$C_sH_{2s+1}$ (M and l have the same meanings as mentioned above, and y and s are each independently 1 to 20). Also, since r is 0 to 20, —$C_rH_{2r+1}$ is hydrogen or an alkyl group with 1 to 20 carbons, and since s is 1 to 20, —$C_sH_{2s+1}$ is an alkyl group with 1 to 20 carbons, and since l is 0 to 20, —$C_lH_{2l}$— is a single bond or an alkylene group with 1 to 20 carbons. The alkyl groups with 1 to 20 carbons and the alkylene group with 1 to 20 carbons are as described above. In addition, two $R^{15}$ and $R^{16}$ may be the same or different.

<<Silane Compound with Structure Represented by the Formula (III)>>

In the formula (III), $A^1$, $R^{15}$ and $R^{16}$ have the same meanings as mentioned above. In addition, two $R^{15}$ may be the same or different.

<<Mixture>>

The silane compound (C) may be a mixture of the silane compound represented by the above formula (II) and the compound with the structure represented by the formula (III). The mixing ratio can be arbitrarily selected depending on the solubility of a compound, the application and the purpose of a silane coupling agent and the like. Typically, it can be within a range of 99:1 to 10:90, and is preferable to be within a range of 99:1 to 50:50.

<<<Specific Examples of Silane Compound (C)>>>

Specific examples of the silane compound (C) include, for example, 3-octanoylthio-propyl(monodimethylaminoethoxy)dimethoxysilane, 3-octanoylthio-propyl (didimethylaminoethoxy)monomethoxysilane, 3-octanoylthio-propyl tridimethylaminoethoxysilane, 3-octanoylthio-propyl (monodiethylaminoethoxy)dimethoxysilane, 3-octanoylthio-propyl(didiethylaminoethoxy)monomethoxysilane, 3-octanoylthio-propyl tridiethylaminoethoxysilane, 3-octanoylthio-propyl(dimethylaminoethoxy)methoxy methylsilane, 3-octanoylthio-propyl(dimethylaminoethoxy) dimethylsilane, 3-octanoylthio-propyl(didimethylaminoethoxy)monomethylsilane, 3-octanoylthio-propyl(diethylaminoethoxy)methoxy methylsilane, 3-octanoylthio-propyl (diethylaminoethoxy)dimethylsilane, 3-octanoylthio-propyl (didiethylaminoethoxy)monomethylsilane, 3-octanoylthio-propyl(methoxy)1,3-dioxa-6-methylaza-2-silacyclooctane, 3-octanoylthio-propyl(methoxy)1,3-dioxa-6-ethylaza-2-silacyclooctane, 3-octanoylthio-propyl(methoxy)1,3-dioxa-6-propylaza-2-silacyclooctane, 3-octanoylthio-propyl(methoxy)1,3-dioxa-6-butylaza-2-silacyclooctane, 3-octanoylthio-propyl(methoxy)1,3-dioxa-6-dodecylaza-2-silacyclooctane, 3-octanoylthio-propyl(methyl)1,3-dioxa-6-methylaza-2-silacyclooctane, 3-octanoylthio-propyl(methyl)1,3-dioxa-6-ethylaza-2-silacyclooctane, 3-octanoylthio-propyl(methyl)1,3-dioxa-6-propylaza-2-silacyclooctane, 3-octanoylthio-propyl(methyl)1,3-dioxa-6-butylaza-2-silacyclooctane, 3-octanoylthio-propyl(methyl)1,3-dioxa-6-dodecylaza-2-silacyclooctane, 3-ethylxanthogenate-propyl(monodimethylaminoethoxy) dimethoxysilane, 3-ethylxanthogenate-propyl(didimethylaminoethoxy)monomethoxysilane, 3-ethylxanthogenate-propyl tridimethylaminoethoxysilane, 3-ethylxanthogenate-propyl(monodiethylaminoethoxy)dimethoxysilane, 3-ethylxanthogenate-propyl(didiethylaminoethoxy) monomethoxysilane, 3-ethylxanthogenate-propyl tridiethylaminoethoxysilane, 3-ethylxanthogenate-propyl(dimethylaminoethoxy)methoxy methylsilane, 3-ethylxanthogenate-propyl(dimethylaminoethoxy)dimethylsilane, 3-ethylxanthogenate-propyl(didimethylaminoethoxy) monomethylsilane, 3-ethylxanthogenate-propyl(diethylaminoethoxy)methoxy methylsilane, 3-ethylxanthogenate-propyl(diethylaminoethoxy)dimethylsilane, 3-ethylxanthogenate-propyl(didiethylaminoethoxy)monomethylsilane, 3-ethylxanthogenate-propyl(methoxy)1,3-dioxa-6-methylaza-2-silacyclooctane, 3-ethylxanthogenate-propyl(methoxy)1,3-dioxa-6-ethylaza-2-silacyclooctane, 3-ethylxanthogenate-propyl(methoxy)1,3-dioxa-6-propylaza-2-silacyclooctane, 3-ethylxanthogenate-propyl(methoxy)1,3-dioxa-6-butylaza-2-silacyclooctane, 3-ethylxanthogenate-propyl(methoxy)1,3-dioxa-6-dodecylaza-2-silacyclooctane, 3-ethylxanthogenate-propyl(methyl)1,3-dioxa-6-methylaza-2-silacyclooctane, 3-ethylxanthogenate-propyl(methyl)1,3-dioxa-6-ethylaza-2-silacyclooctane, 3-ethylxanthogenate-propyl(methyl)1,3-dioxa-6-propylaza-2-silacyclooctane, 3-ethylxanthogenate-propyl(methyl)1,3-dioxa-6-butylaza-2-silacyclooctane, 3-ethylxanthogenate-propyl(methyl)1,3-dioxa-6-dodecylaza-2-silacyclooctane, 3-phenoxyethanoylthio-propyl(monodimethylaminoethoxy) dimethoxysilane, 3-phenoxyethanoylthio-propyl(didimethylaminoethoxy)monomethoxysilane, 3-phenoxyethanoylthio-propyl tridimethylaminoethoxysilane, 3-phenoxyethanoylthio-propyl(monodiethylaminoethoxy) dimethoxysilane, 3-phenoxyethanoylthio-propyl(didiethylaminoethoxy)monomethoxysilane, 3-phenoxyethanoylthio-propyl tridiethylaminoethoxysilane, 3-phenoxyethanoylthio-propyl(dimethylaminoethoxy)methoxy methylsilane, 3-phenoxyethanoylthio-propyl(dimethylaminoethoxy) dimethylsilane, 3-phenoxyethanoylthio-propyl(didimethylaminoethoxy)monomethylsilane, 3-phenoxyethanoylthio-propyl(diethylaminoethoxy)methoxy methylsilane, 3-phenoxyethanoylthio-propyl(diethylaminoethoxy)dimethylsilane, 3-phenoxyethanoylthio-propyl(didiethylaminoethoxy)monomethylsilane, 3-phenoxyethanoylthio-propyl(methoxy)1,3-dioxa-6-methylaza-2-silacyclooctane, 3-phenoxyethanoylthio-propyl(methoxy)1,3-dioxa-6-ethylaza-2-silacyclooctane, 3-phenoxyethanoylthio-propyl(methoxy)1,3-dioxa-6-propylaza-2-silacyclooctane, 3-phenoxyethanoylthio-propyl(methoxy)1,3-dioxa-6-butylaza-2-silacyclooctane, 3-phenoxyethanoylthio-propyl(methoxy)1,3-dioxa-6-dodecylaza-2-silacyclooctane, 3-phenoxyethanoylthio-propyl(methyl)1,3-dioxa-6-methylaza-2-silacyclooctane, 3-phenoxyethanoylthio-propyl(methyl)1,3-dioxa-6-ethylaza-2-silacyclooctane, 3-phenoxyethanoylthio-propyl(methyl)1,3-dioxa-6-propylaza-2-silacyclooctane, 3-phenoxyethanoylthio-propyl(methyl)1,3-dioxa-6-butylaza-2-silacyclooctane, 3-phenoxyethanoylthio-propyl(methyl)1,3-dioxa-6-dodecylaza-2-silacyclooctane, 3-ethyloxalylthio-propyl(monodimethylaminoethoxy)dimethoxysilane, 3-ethyloxalylthio-propyl(didimethylaminoethoxy)monomethoxysilane, 3-ethyloxalylthio-propyl tridimethylaminoethoxysilane, 3-ethyloxalylthio-propyl (monodiethylaminoethoxy) dimethoxysilane, 3-ethyloxalylthio-propyl (didiethylaminoethoxy)monomethoxysilane, 3-ethyloxalylthio-propyl tridiethylaminoethoxysilane, 3-ethyloxalylthio-propyl (dimethylaminoethoxy)methoxy methylsilane, 3-ethyloxalylthio-propyl(dimethylaminoethoxy)dimethylsilane, 3-ethyloxalylthio-propyl(didimethylaminoethoxy) monomethylsilane, 3-ethyloxalylthio-propyl(diethylaminoethoxy)methoxy methylsilane, 3-ethyloxalylthio-propyl (diethylaminoethoxy)dimethylsilane, 3-ethyloxalylthio-propyl(didiethylaminoethoxy)monomethylsilane, 3-ethyloxalylthio-propyl(methoxy)1,3-dioxa-6-methylaza-2-silacyclooctane, 3-ethyloxalylthio-propyl(methoxy)1,3-dioxa-6-ethylaza-2-silacyclooctane, 3-ethyloxalylthio-propyl(methoxy)1,3-dioxa-6-propylaza-2-silacyclooctane, 3-ethyloxalylthio-propyl(methoxy)1,3-dioxa-6-butylaza-2-silacyclooctane, 3-ethyloxalylthio-propyl(methoxy)1,3-dioxa-6-dodecylaza-2-silcyclooctane, 3-ethyloxalylthio-propyl(methyl)1,3-dioxa-6-methylaza-2-silacyclooctane, 3-ethyloxalylthio-propyl(methyl)1,3-dioxa-6-ethylaza-2-silacyclooctane, 3-ethyloxalylthio-propyl(methyl)1,3-dioxa-6-propylaza-2-silacyclooctane, 3-ethyloxalylthio-propyl (methyl)1,3-dioxa-6-butylaza-2-silacyclooctane, 3-ethyloxalylthio-propyl(methyl)1,3-dioxa-6-dodecylaza-2-silacyclooctane, bis(3-(monodimethylaminoethoxy) dimethoxysilyl-propyl)disulfide, bis(3-(didimethylaminoethoxy)monomethoxysilyl-propyl)disulfide, bis(3-(tridimethylaminoethoxy)silyl-propyl)disulfide, bis(3-(monodiethylaminoethoxy)dimethoxysilyl-propyl)disulfide, bis(3-(didiethylaminoethoxy)monomethoxysilyl-propyl) disulfide, bis(3-(tridiethylaminoethoxy)silyl-propyl)disulfide, bis(3-(dimethylaminoethoxy)methoxymethylsilyl-propyl)disulfide, bis(3-(dimethylaminoethoxy)dimethylsilyl-propyl)disulfide, bis(3-(didimethylaminoethoxy) monomethylsilyl-propyl)disulfide, bis(3-(diethylaminoethoxy)methoxymethylsilyl-propyl)disulfide, bis(3-(diethylaminoethoxy)dimethylsilyl-propyl)disulfide, bis(3-(didiethylaminoethoxy)monomethylsilyl-propyl)disulfide, bis(3-(methoxy)1,3-dioxa-6-methylaza-2-silacyclooctyl-propyl)disulfide, bis(3-(methoxy)1,3-dioxa-6-ethylaza-2-silacyclooctyl-propyl)disulfide, bis(3-(methoxy)1,3-dioxa-6-propylaza-2-silacyclooctyl-propyl)disulfide, bis(3-(methoxy)1,3-dioxa-6-butylaza-2-silacyclooctyl-propyl)disulfide, bis(3-(methoxy)1,3-dioxa-6-dodecylaza-2-silacyclooctyl-propyl)disulfide, bis(3-(methyl)1,3-dioxa-6-methylaza-2-silacyclooctyl-propyl)disulfide, bis(3-(methyl)1,3-dioxa-6-ethylaza-2-silacyclooctyl-propyl)disulfide, bis(3-(methyl)1,3-dioxa-6-propylaza-2-silacyclooctyl-propyl)disulfide, bis(3-(methyl)1,3-dioxa-6-butylaza-2-silacyclooctyl-propyl)disulfide, bis(3-(methyl)1,3-dioxa-6-dodecylaza-2-silacyclooctyl-propyl)disulfide, bis(3-(monodimethylaminoethoxy)dimethoxysilyl-propyl)tetrasulfide, bis(3-(didimethylaminoethoxy)monomethoxysilyl-propyl)tetrasulfide, bis(3-(tridimethylaminoethoxy)silyl-propyl)tetrasulfide, bis(3-(monodiethylaminoethoxy)dimethoxysilyl-propyl)tetrasulfide, bis(3-(didiethylaminoethoxy)monomethoxysilyl-propyl)tetrasulfide, bis(3-(tridiethylaminoethoxy)silyl-propyl)tetrasulfide, bis(3-(dimethylaminoethoxy)methoxymethylsilyl-propyl)tetrasulfide, bis(3-(dimethylaminoethoxy)dimethylsilyl-propyl)tetrasulfide, bis(3-(didimethylaminoethoxy)monomethylsilyl-propyl)tetrasulfide, bis(3-(diethylaminoethoxy)methoxymethylsilyl-propyl)tetrasulfide, bis(3-(diethylaminoethoxy)dimethylsilyl-propyl)tetrasulfide, bis(3-(didiethylaminoethoxy)monomethylsilyl-propyl)tetrasulfide, bis(3-(methoxy)1,3-dioxa-6-methylaza-2-silacyclooctyl-propyl)tetrasulfide, bis(3-(methoxy)1,3-dioxa-6-ethylaza-2-silacyclooctyl-propyl)tetrasulfide, bis(3-(methoxy)1,3-dioxa-6-propylaza-2-silacyclooctyl-propyl)tetrasulfide, bis(3-(methoxy)1,3-dioxa-6-butylaza-2-silacyclooctyl-propyl)tetrasulfide, bis(3-(methoxy)1,3-dioxa-6-dodecylaza-2-silacyclooctyl-propyl)tetrasulfide, bis(3-(methyl)1,3-dioxa-6-methylaza-2-silacyclooctyl-propyl)tetrasulfide, bis(3-(methyl)1,3-dioxa-6-ethylaza-2-silacyclooctyl-propyl)tetrasulfide, bis(3-(methyl)1,3-dioxa-6-propylaza-2-silacyclooctyl-propyl)tetrasulfide, bis(3-(methyl)1,3-dioxa-6-butylaza-2-silacyclooctyl-propyl)tetrasulfide, bis(3-(methyl)1,3-dioxa-6-dodecylaza-2-silacyclooctyl-propyl)tetrasulfide, tri(dimethylaminoethoxy)silane, tri(diethylaminoethoxy)silane, tri(dibutylaminoethoxy)silane, di(dimethylaminoethoxy)methylsilane, di(dimethylaminoethoxy)methoxysilane, di(dimethylaminoethoxy)ethoxysilane, (dimethylaminoethoxy)diethoxysilane, (dimethylaminoethoxy)methyl ethoxysilane, 1,3-dioxa-6-methylaza-2-ethoxysila-cyclooctane, 1,3-dioxa-6-methylaza-2-methylsila-cyclooctane, 1,3-dioxa-6-butylaza-2-ethoxylsila-cyclooctane, 1,3-dioxa-6-butylaza-2-methylsila-cyclooctane, tri(dimethylaminoethoxy)silylpropyl chloride, tri(diethylaminoethoxy)silylpropyl chloride, tri(dibutylaminoethoxy)silylpropyl chloride, di(dimethylaminoethoxy)methylsilylpropyl chloride, di(dimethylaminoethoxy)methoxysilylpropyl chloride, di(dimethylaminoethoxy)ethoxysilylpropyl chloride, (dimethylaminoethoxy)diethoxysilylpropyl chloride, (dimethylaminoethoxy)methylethoxysilypropyl chloride, 1,3-dioxa-6-methylaza-2-ethoxysila-cyclooctylpropyl chloride, 1,3-dioxa-6-methylaza-2-methylsila-cyclooctylpropyl chloride, 1,3-dioxa-6-butylaza-2-ethoxysila-cyclooctylpropyl chloride, 1,3-dioxa-6-butylaza-2-methylsila-cyclooctylpropyl chloride and the like.

EXAMPLES

The invention will be described in further detail with reference to examples below, but the invention should not be limited to any of the following examples.

Comparative Example 1

Production of Silane Compound (C) Using Base Catalyst 18.0 g of 3-mercaptopropyl dimethoxy methylsilane, 11.9 g of N-methyldiethanolamine, and 0.05 g of potassium hydroxide were dissolved in 200 mL of xylene under a nitrogen atmosphere in a 500 mL four-neck recovery flask. It was heated to 150° C., and stirred for 10 hours. Subsequently, a solvent was removed by a rotary evaporator at 20 hPa/40° C., and then a fraction with a boiling point of 150 to 160° C. was isolated by distillation under reduced pressure using a rotary pump (10 Pa) and a cold trap (dry ice+ethanol) to obtain 10.5 g of a silane compound (C). As the silane compound (C) was analyzed with $^1$H-NMR (CDCl3, 700 MHz), the result of $^1$H-NMR (δ; ppm)=3.7 (m; 4H), 2.6 (t; 4H), 2.5 (m; 2H), 2.4 (s; 3H), 1.6 (m; 2H), 0.6 (t; 2H), 0.1 (s; 3H) was obtained and it was found out to be 3-mercaptopropyl(methyl)1,3-dioxa-6-methylaza-2-silacyclooctane as the silane compound (C).

Comparative Example 2

Production of Silane Compound (C) Using Acid Catalyst 23.6 g of 3-mercaptopropyl dipropoxy methylsilane, 11.9 g of N-methyldiethanolamine, and 0.05 g of p-toluenesulfonic acid were dissolved in 200 mL of xylene under a nitrogen atmosphere in a 500 mL four-neck recovery flask. It was heated to 150° C., and stirred for 12 hours. However, disappearance of raw materials was not observed, and the reaction did not progress.

Example 1

Production of Silane Compound (C) Using Metal-Containing Catalyst 18.0 g of 3-mercaptopropyl dimethoxy methylsilane, 11.9 g of N-methyldiethanolamine, and 0.05 g of aluminum triethoxide were dissolved in 200 mL of xylene under a nitrogen atmosphere in a 500 mL four-neck recovery flask. It was heated to 150° C., and stirred for 1 hour. Subsequently, a solvent was removed by a rotary evaporator at 20 hPa/40° C., and then remaining volatiles were removed with a rotary pump (10 Pa) and a cold trap (dry ice+ethanol) to obtain 21.6 g of a silane compound (C). As the silane compound (C) was analyzed with $^1$H-NMR (CDCl3, 700 MHz), the result of $^1$H-NMR (δ; ppm)=3.7 (m; 4H), 2.6 (t; 4H), 2.5 (m; 2H), 2.4 (s; 3H), 1.6 (m; 2H), 0.6 (t; 2H), 0.1 (s; 3H) was obtained and it was found out to be 3-mercaptopropyl(methyl)1,3-dioxa-6-methylaza-2-silacyclooctane as the silane compound (C).

Example 2

Production of Silane Compound (C) Using Metal-Containing Catalyst 18.0 g of 3-mercaptopropyl dimethoxy methylsilane, 11.9 g of N-methyldiethanolamine, and 0.05 g of titanium tetrabutoxide were dissolved in 200 mL of xylene under a nitrogen atmosphere in a 500 mL four-neck recovery flask. It was heated to 150° C., and stirred for 3 hours. Subsequently, a solvent was removed by a rotary evaporator at 20 hPa/40° C., and then remaining volatiles were removed with a rotary pump (10 Pa) and a cold trap (dry ice+ethanol) to obtain 21.6 g of a silane compound (C). As the silane compound (C) was analyzed with $^1$H-NMR (CDCl3, 700 MHz), the result of $^1$H-NMR (δ; ppm)=3.7 (m; 4H), 2.6 (t; 4H), 2.5 (m; 2H), 2.4 (s; 3H), 1.6 (m; 2H), 0.6 (t; 2H), 0.1 (s; 3H) was obtained and it was found out to be 3-mercaptopropyl(methyl)1,3-dioxa-6-methylaza-2-silacyclooctane as the silane compound (C).

Example 3

Production of Silane Compound (C) Using Metal-Containing Catalyst 18.0 g of 3-mercaptopropyl dimethoxy methylsilane, 11.9 g of N-methyldiethanolamine, and 0.05 g of aluminum tri-n-butoxide were dissolved under a nitrogen atmosphere in a 500 mL four-neck recovery flask. It was heated to 150° C., and stirred for 2 hours. Subsequently, a solvent was removed by a rotary evaporator at 20 hPa/40° C., and then remaining volatiles were removed with a rotary pump (10 Pa) and a cold trap (dry ice+ethanol) to obtain 21.4 g of a silane compound (C). As the silane compound (C) was analyzed with $^1$H-NMR (CDCl3, 700 MHz), the result of $^1$H-NMR (δ; ppm)=3.7 (m; 4H), 2.6 (t; 4H), 2.5 (m; 2H), 2.4 (s; 3H), 1.6 (m; 2H), 0.6 (t; 2H), 0.1 (s; 3H) was obtained and it was found out to be 3-mercaptopropyl(methyl)1,3-dioxa-6-methylaza-2-silacyclooctane as the silane compound (C).

Example 4

Production of Silane Compound (C) Using Metal-Containing Catalyst 22.1 g of 3-ethylxanthogenate-propyl dimethoxy methylsilane, 9.8 g of N-methyldiethanolamine, and 0.05 g of aluminum tri-t-butoxide were dissolved in 200 mL of xylene under a nitrogen atmosphere in a 500 mL four-neck recovery flask. It was heated to 150° C., and stirred for 2 hours. Subsequently, a solvent was removed by a rotary evaporator at 20 hPa/40° C., and then remaining volatiles were removed with a rotary pump (10 Pa) and a cold trap (dry ice+ethanol) to obtain 25.0 g of a silane compound (C). As the silane compound (C) was analyzed with $^1$H-NMR (CDCl3, 700 MHz), the result of $^1$H-NMR (δ; ppm)=4.6 (m; 2H), 3.8 (m; 4H), 3.1 (t; 2H), 2.5 (m; 4H), 2.4 (s; 3H), 1.8 (m; 2H), 1.4 (m; 3H), 0.7 (t; 2H), 0.1 (s; 3H) was obtained and it was found out to be 3-ethylxanthogenate-propyl(methyl)1,3-dioxa-6-methylaza-2-silacyclooctane as the silane compound (C).

Example 5

Production of Silane Compound (C) Using Metal-Containing Catalyst 26.2 g of 3-ethyloxalylthio-propyl dimethoxy methylsilane, 9.8 g of N-methyldiethanolamine, and 0.05 g of aluminum triisopropoxide were dissolved in 200 mL of xylene under a nitrogen atmosphere in a 500 mL four-neck recovery flask. It was heated to 150° C., and stirred for 2 hours. Subsequently, a solvent was removed by a rotary evaporator at 20 hPa/40° C., and then remaining volatiles were removed with a rotary pump (10 Pa) and a cold trap (dry ice+ethanol) to obtain 27.5 g of a silane compound (C). As the silane compound (C) was analyzed with $^1$H-NMR (CDCl3, 700 MHz), the result of $^1$H-NMR (δ; ppm)=4.3 (m; 2H), 3.8 (m; 4H), 2.8 (t; 2H), 2.5 (m; 4H), 2.4 (m; 3H), 1.6 (m; 2H), 1.3 (t; 3H), 0.6 (t; 2H), 0.1 (t; 3H) was obtained and it was found out to be 3-ethyloxalylthio-propyl(methyl)1,3-dioxa-6-methylaza-2-silacyclooctane as the silane compound (C).

The invention claimed is:

1. A process for producing a silane coupling agent, comprising a step of reacting a silane compound (A) with a compound (B), in the presence of a metal-containing catalyst (m) to obtain a silane compound (C), wherein the silane compound (A) is represented by the following general formula (IV):

(IV)

wherein in the formula IV, at least one of $R'^1$, $R'^2$ and $R'^3$ is represented by $O-C_LH_{2L+1}$ or X, and the other is represented by $-(M-C_LH_{2L})_y C_s H_{2s+1}$, wherein X is F, Cl, Br or I, M is $-O-$ or $-CH_2-$, L and y are each independently 0 to 20, and s is 1 to 20, provided that in one or more of $R'^1$, $R'^2$ and $R'^3$, M is $-O-$, and $A'^1$ is represented by the following formula (IVa) or formula (IVb):

(IVa)

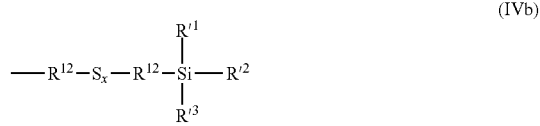

(IVb)

wherein $A^2$ is $-S-CO-R^{13}$, $-S-S-R^{13}$, $-S-CS-O-R^{13}$, $-R^{14}-Cl$, $-R^{14}-Br$, $-SH$, $-S-CO-O-R^{13}$ or $-S-CO-CO-R^{13}$, provided that $R^{12}$ is $-C_tH_{2t}-$, $R^{13}$ is $-C_rH_{2r+1}$, $R^{14}$ is $-C_tH_{2t}-$, r and t are each independently 0 to 20, x is 1 to 10, and $R'^1$, $R'^2$ and $R'^3$ have the same meaning as defined above;

the compound (B) is selected from the group consisting of dimethylaminoethanol, diethylaminoethanol, dibutylaminoethanol, N-methyldiethanolamine, N-butyldiethanolamine, and N-lauryldiethanolamine;

the silane compound (C) is represented by the following general formula (I):

(I)

wherein in the formula (I), at least one of $R^1$, $R^2$ and $R^3$ is represented by the following general formula (Ia) or formula (Ib):

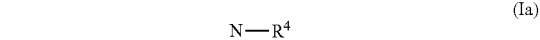

(Ia)

(Ib)

and the other is represented by -M-C$_L$H$_{2L+}$or -(M-C$_L$H$_{2L}$)$_y$ C$_s$H$_{2s+1}$, wherein M is —O— or —CH$_2$—, X and Y are each independently —O—, —NR$^6$— or —CH$_2$—, R$^4$ is —OR$^6$, —NR$^6$R$^7$ or —R$^6$, and R$^5$ is —NR$^6$R$^7$, —NR$^6$—NR$^6$R$^7$ or —N=NR$^6$, provided that R$^6$ is —C$_n$H$_{2n+1}$, R$^7$ is —C$_q$H$_{2q+1}$, and L, m, n and q are each independently 0 to 20, and y and s are each independently 1 to 20, provided that in one or more of R$^1$, R$^2$ and R$^3$, M is —O—, and A$^1$ is represented by the following general formula (Ic), formula (Id) or formula (Ie):

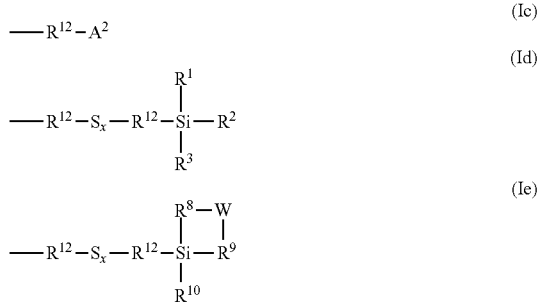

wherein R$^1$, R$^2$ and R$^3$ have the same meanings as defined above, and A$^2$ is —S—CO—R$^{13}$, —S—S—R$^{13}$, —S—CS—O—R$^{13}$, —R$^{14}$—Cl, —R$^{14}$—Br, —SH, —S—CO—O—R$^{13}$, or —S—CO—CO—R$^{13}$, provided that R$^{12}$ is —C$_r$H$_{2t}$—, R$^{13}$ is —C$_r$H$_{2r+1}$, R$^{14}$ is —C$_r$H$_{2t}$—, r and t are each independently 0 to 20, x is 1 to 10, W is represented by —NR$^6$—, —O— or —CR$^6$R$^{11}$—, R$^8$ and R$^9$ are each independently represented by -M-C$_L$H$_{2L}$—, R$^{11}$ is —R$^7$ or —C$_m$H$_{2m}$—R$^5$, R$^{10}$ is represented by -M-C$_L$H$_{2L+1}$ or -M-C$_L$H$_{2L}$—R$^5$ or -(M-C$_L$H$_{2L}$)$_y$C$_s$H$_{2s+1}$, and R$^5$, R$^6$, R$^7$, M, L, m, n, q, y and s have the same meaning as defined above;
or the following general formula (II):

wherein in the formula (II), R$^{15}$ is represented by —C$_L$H$_{2L}$—, and R$^{16}$ is represented by -M-C$_r$H$_{2r+1}$ or -(M-C$_L$H$_{2L}$)$_y$C$_s$H$_{2s+1}$, two R$^{15}$ may be the same or different, two R$^{16}$ may be the same or different, and A$^1$, M, L, r, y and s have the same meanings as define above; and the metal-containing catalyst (m) is an aluminum alkoxide.

2. A process for producing a silane coupling agent according to claim 1, wherein a reaction temperature in the presence of the metal catalyst (m) is within a range of 50 to 200° C.

3. A process for producing a silane coupling agent according to claim 2, wherein the reaction temperature in the presence of the metal catalyst (m) is within a range of 90 to 170° C.

4. A process for producing a silane coupling agent according to claim 1, wherein a reaction time in the presence of the metal catalyst (m) is within a range of 0.5 to 6 hours.

5. A process for producing a silane coupling agent according to claim 1, wherein the silane compound (C) is represented by the general formula (II).

6. A process for producing a silane coupling agent according to claim 1, wherein the silane compound (C) is selected from the group consisting of 3-octanoylthio-propyl(monodimethylaminoethoxy)dimethoxysilane, 3-octanoylthio-propyl (didimethylaminoethoxy)monomethoxysilane, 3-octanoylthio-propyl tridimethylaminoethoxysilane, 3-octanoylthio-propyl(monodiethylaminoethoxy) dimethoxysilane, 3-octanoylthio-propyl(didiethylaminoethoxy) monomethoxysilane, 3-octanoylthio-propyl tridiethylaminoethoxysilane, 3-octanoylthio-propyl(dimethylaminoethoxy) methoxy methylsilane, 3-octanoylthio-propyl(dimethylaminoethoxy)dimethylsilane, 3-octanoylthio-propyl(didimethylaminoethoxy)monomethylsilane, 3-octanoylthio-propyl (diethylaminoethoxy) methoxy methylsilane, 3-octanoylthio-propyl(diethylaminoethoxy)dimethylsilane, 3-octanoylthio-propyl(didiethylaminoethoxy)monomethylsilane, 3-octanoylthio-propyl(methoxy)1,3-dioxa-6-methylaza-2-silacyclooctane, 3-octanoylthio-propyl (methoxy) 1,3-dioxa-6-ethylaza-2-silacyclooctane, 3-octanoylthio-propyl(methoxy)1,3-dioxa-6-propylaza-2-silacyclooctane, 3-octanoylthio-propyl(methoxy)1,3-dioxa-6-butylaza-2-silacyclooctane, 3-octanoylthio-propyl(methoxy)1,3-dioxa-6-dodecylaza-2-silacyclooctane, 3-octanoylthio-propyl(methyl)1,3-dioxa-6-methylaza-2-silacyclooctane, 3-octanoylthio-propyl(methyl)1,3-dioxa-6-ethylaza-2-silacyclooctane, 3-octanoylthio-propyl(methyl)1,3-dioxa-6-propylaza-2-silacyclooctane, 3-octanoylthio-propyl(methyl)1,3-dioxa-6-butylaza-2-silacyclooctane, 3-octanoylthio-propyl(methyl)1,3-dioxa-6-dodecylaza-2-silacyclooctane, 3-ethylxanthogenate-propyl(monodimethylaminoethoxy) dimethoxysilane, 3-ethylxanthogenate-propyl(didimethylaminoethoxy)monomethoxysilane, 3-ethylxanthogenate-propyl tridimethylaminoethoxysilane, 3-ethylxanthogenate-propyl(monodiethylaminoethoxy)dimethoxysilane, 3-ethylxanthogenate-propyl(didiethylaminoethoxy) monomethoxysilane, 3-ethylxanthogenate-propyl tridiethylaminoethoxysilane, 3-ethylxanthogenate-propyl (dimethylaminoethoxy) methoxy methylsilane, 3-ethylxanthogenate-propyl (dimethylaminoethoxy)dimethylsilane, 3-ethylxanthogenate-propyl(didimethylaminoethoxy) monomethylsilane, 3-ethylxanthogenate-propyl(diethylaminoethoxy)methoxy methylsilane, 3-ethylxanthogenate-propyl(diethylaminoethoxy)dimethylsilane, 3-ethylxanthogenate-propyl (didiethylaminoethoxy) monomethylsilane, 3-ethylxanthogenate-propyl(methoxy)1,3-dioxa-6-methylaza-2-silacyclooctane, 3-ethylxanthogenate-propyl(methoxy)1,3-dioxa-6-ethylaza-2-silacyclooctane, 3-ethylxanthogenate-propyl(methoxy)1,3-dioxa-6-propylaza-2-silacyclooctane, 3-ethylxanthogenate-propyl (methoxy)1,3-dioxa-6-butylaza-2-silacyclooctane, 3-ethylxanthogenate-propyl(methoxy)1,3-dioxa-6-dodecylaza-2-silacyclooctane, 3-ethylxanthogenate-propyl(methyl) 1,3-dioxa-6-methylaza-2-silacyclooctane, 3-ethylxanthogenate-propyl(methyl)1,3-dioxa-6-ethylaza-2-silacyclooctane, 3-ethylxanthogenate-propyl(methyl)1,3-dioxa-6-propylaza-2-silacyclooctane, 3-ethylxanthogenate-propyl(methyl)1,3-dioxa-6-butylaza-2-silacyclooctane, 3-ethylxanthogenate-propyl(methyl)1,3-dioxa-6-dodecylaza-2-silacyclooctane, 3-ethyloxalylthio-propyl(monodimethylaminoethoxy) dimethoxysilane, 3-ethyloxalylthio-propyl(didimethylaminoethoxy)monomethoxysilane, 3-ethyloxalylthio-propyl tridimethylaminoethoxysilane, 3-ethyloxalylthio-propyl (monodiethylaminoethoxy)dimethoxysilane, 3-ethyloxalylthio-propyl(didiethylaminoethoxy)

monomethoxysilane, 3-ethyloxalylthio-propyl tridiethylaminoethoxysilane, 3-ethyloxalylthio-propyl (dimethylaminoethoxy) methoxy methylsilane, 3-ethyloxalylthio-propyl (dimethylaminoethoxy) dimethylsilane, 3-ethyloxalylthio-propyl(didimethylaminoethoxy) monomethylsilane, 3-ethyloxalylthio-propyl(diethylaminoethoxy) methoxy methylsilane, 3-ethyloxalylthio-propyl (diethylaminoethoxy) dimethylsilane, 3-ethyloxalylthio-propyl(didiethylaminoethoxy) monomethylsilane, 3-ethyloxalylthio-propyl (methoxy)1,3-dioxa-6-methylaza-2-silacyclooctane, 3-ethyloxalylthio-propyl(methoxy)1,3-dioxa-6-ethylaza-2-silacyclooctane, 3-ethyloxalylthio-propyl(methoxy)1,3-dioxa-6-propylaza-2-silacyclooctane, 3-ethyloxalylthio-propyl (methoxy) 1,3-dioxa-6-butylaza-2-silacyclooctane, 3-ethyloxalylthio-propyl(methoxy)1,3-dioxa-6-dodecylaza-2-silcyclooctane, 3-ethyloxalylthio-propyl(methyl)1,3-dioxa-6-methylaza-2-silacyclooctane, 3-ethyloxalylthio-propyl(methyl)1,3-dioxa-6-ethylaza-2-silacyclooctane, 3-ethyloxalylthio-propyl(methyl)1,3-dioxa-6-propylaza-2-silacyclooctane, 3-ethyloxalylthio-propyl(methyl)1,3-dioxa-6-butylaza-2-silacyclooctane, 3-ethyloxalylthio-propyl (methyl) 1,3-dioxa-6-dodecylaza-2-silacyclooctane, bis(3-(monodimethylaminoethoxy)dimethoxysilyl-propyl) disulfide, bis(3-(didimethylaminoethoxy)monomethoxysilyl-propyl) disulfide, bis(3-(tridimethylaminoethoxy)silyl-propyl) disulfide, bis(3-(monodiethylaminoethoxy)dimethoxysilyl-propyl)disulfide, bis(3-(didiethylaminoethoxy)monomethoxysilyl-propyl)disulfide, bis(3-(tridiethylaminoethoxy)silyl-propyl) disulfide, bis(3-(dimethylaminoethoxy)methoxymethylsilyl-propyl) disulfide, bis(3-(dimethylaminoethoxy)dimethylsilyl-propyl)disulfide, bis(3-(didimethylaminoethoxy)monomethylsilyl-propyl)disulfide, bis(3-(diethylaminoethoxy)methoxymethylsilyl-propyl)disulfide, bis(3-(diethylaminoethoxy)dimethylsilyl-propyl)disulfide, bis(3-(didiethylaminoethoxy)monomethylsilyl-propyl)disulfide, bis(3-(methoxy)1,3-dioxa-6-methylaza-2-silacyclooctyl-propyl)disulfide, bis(3-(methoxy)1,3-dioxa-6-ethylaza-2-silacyclooctyl-propyl)disulfide, bis(3-(methoxy)1,3-dioxa-6-propylaza-2-silacyclooctyl-propyl) disulfide, bis(3-(methoxy)1,3-dioxa-6-butylaza-2-silacyclooctyl-propyl) disulfide, bis(3-(methoxy)1,3-dioxa-6-dodecylaza-2-silacyclooctyl-propyl)disulfide, bis(3-(methyl)1,3-dioxa-6-methylaza-2-silacyclooctyl-propyl)disulfide, bis(3-(methyl)1,3-dioxa-6-ethylaza-2-silacyclooctyl-propyl)disulfide, bis(3-(methyl)1,3-dioxa-6-propylaza-2-silacyclooctyl-propyl) disulfide, bis(3-(methyl)1,3-dioxa-6-butylaza-2-silacyclooctyl-propyl)disulfide, bis(3-(methyl)1,3-dioxa-6-dodecylaza-2-silacyclooctyl-propyl)disulfide, bis(3-(monodimethylaminoethoxy)dimethoxysilyl-propyl)tetrasulfide, bis(3-(didimethylaminoethoxy)monomethoxysilyl-propyl)tetrasulfide, bis(3-(tridimethylaminoethoxy)silyl-propyl)tetrasulfide, bis(3-(monodiethylaminoethoxy)dimethoxysilyl-propyl)tetrasulfide, bis(3-(didiethylaminoethoxy)monomethoxysilyl-propyl)tetrasulfide, bis(3-(tridiethylaminoethoxy)silyl-propyl)tetrasulfide, bis(3-(dimethylaminoethoxy)methoxymethylsilyl-propyl)tetrasulfide, bis(3-(dimethylaminoethoxy)dimethylsilyl-propyl)tetrasulfide, bis(3-(didimethylaminoethoxy)monomethylsilyl-propyl)tetrasulfide, bis(3-(diethylaminoethoxy)methoxymethylsilyl-propyl)tetrasulfide, bis(3-(diethylaminoethoxy)dimethylsilyl-propyl)tetrasulfide, bis(3-(didiethylaminoethoxy)monomethylsilyl-propyl)tetrasulfide, bis(3-(methoxy)1,3-dioxa-6-methylaza-2-silacyclooctyl-propyl)tetrasulfide, bis(3-(methoxy)1,3-dioxa-6-ethylaza-2-silacyclooctyl-propyl)tetrasulfide, bis(3-(methoxy)1,3-dioxa-6-propylaza-2-silacyclooctyl-propyl) tetrasulfide, bis(3-(methoxy)1,3-dioxa-6-butylaza-2-silacyclooctyl-propyl)tetrasulfide, bis(3-(methoxy)1,3-dioxa-6-dodecylaza-2-silacyclooctyl-propyl) tetrasulfide, bis(3-(methyl)1,3-dioxa-6-methylaza-2-silacyclooctyl-propyl)tetrasulfide, bis(3-(methyl)1,3-dioxa-6-ethylaza-2-silacyclooctyl-propyl)tetrasulfide, bis(3-(methyl)1,3-dioxa-6-propylaza-2-silacyclooctyl-propyl) tetrasulfide, bis(3-(methyl)1,3-dioxa-6-butylaza-2-silacyclooctyl-propyl)tetrasulfide, bis(3-(methyl)1,3-dioxa-6-dodecylaza-2-silacyclooctyl-propyl)tetrasulfide, 1,3-dioxa-6-methylaza-2-ethoxysila-cyclooctane, 1,3-dioxa-6-methylaza-2-methylsila-cyclooctane, 1,3-dioxa-6-butylaza-2-ethoxysila-cyclooctane, 1,3-dioxa-6-butylaza-2-methylsila-cyclooctane, tri(dimethylaminoethoxy) silylpropyl chloride, tri(diethylaminoethoxy)silylpropyl chloride, tri(dibutylaminoethoxy)silylpropyl chloride, di(dimethylaminoethoxy)methylsilylpropyl chloride, di(dimethylaminoethoxy)methoxysilylpropyl chloride, di(dimethylaminoethoxy)ethoxysilypropyl chloride, (dimethylaminoethoxy)diethoxysilylpropyl chloride, (dimethyaminoethoxy)methylethoxysilylpropyl chloride, 1,3-dioxa-6-methylaza-2-ethoxysila-cyclooctylpropyl chloride, 1,3-dioxa-6-methylaza-2-methylsila-cyclooctylpropyl chloride, 1,3-dioxa-6-butylaza-2-ethoxysila-cyclooctylpropyl chloride, and 1,3-dioxa-6-butylaza-2-methylsila-cyclooctylpropyl chloride.

\* \* \* \* \*